Figure 1:
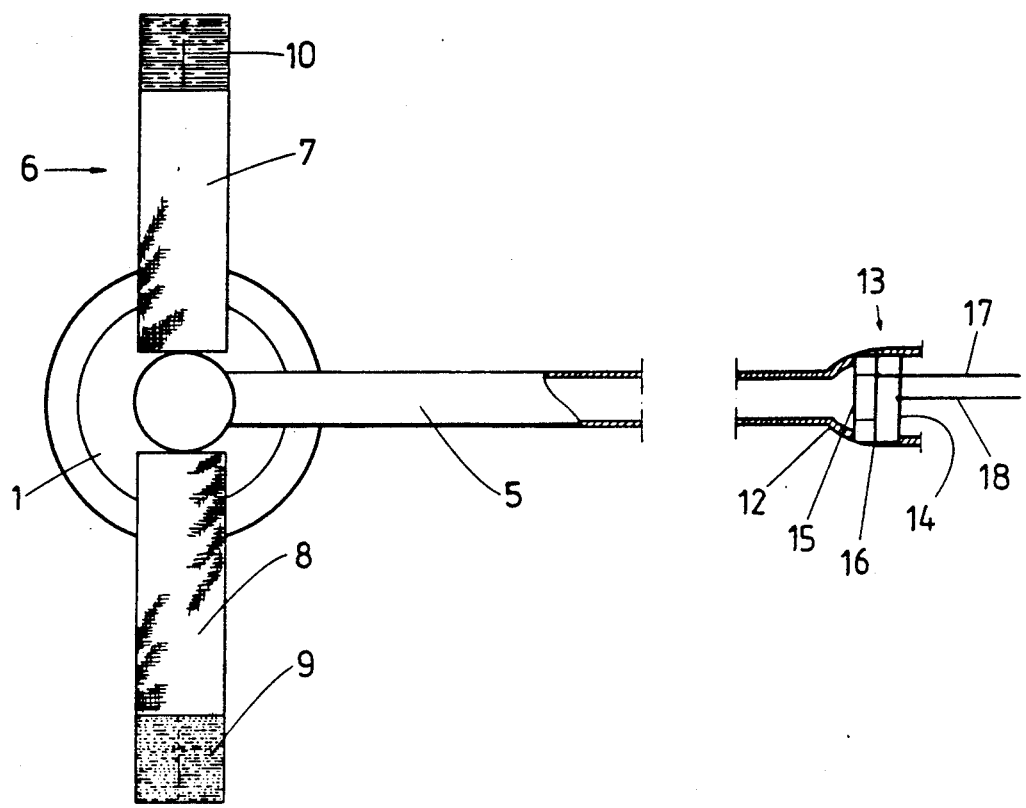

United States Patent [19]

Hök et al.

[11] Patent Number: 5,022,405
[45] Date of Patent: Jun. 11, 1991

[54] STETHOSCOPE FOR USE IN NUCLEAR MAGNETIC RESONANCE DIAGNOSTICS

[75] Inventors: J. Bertil W. Hök, Västerås, Sweden; Valerie Bythell, London, England

[73] Assignee: Hok Instrument AB, Västerås, Sweden

[21] Appl. No.: 196,232

[22] Filed: May 20, 1988

[30] Foreign Application Priority Data

May 25, 1987 [SE] Sweden ................ 8702160

[51] Int. Cl.⁵ .............................. A61B 7/02
[52] U.S. Cl. ................. 128/715; 128/653 A; 128/773; 381/67
[58] Field of Search .............. 128/653 A, 715, 721, 128/773; 381/67, 111, 113, 116; 324/307, 318, 322

[56] References Cited

U.S. PATENT DOCUMENTS

| | | | |
|---|---|---|---|
| 2,699,465 | 1/1955 | Hamilton | 128/715 |
| 3,867,925 | 2/1975 | Ersek | 128/2.05 S |
| 3,999,625 | 12/1976 | Pickett et al. | 128/715 |
| 4,248,241 | 2/1981 | Tacchi | 128/715 |
| 4,528,690 | 7/1985 | Sedgwick | 128/715 |
| 4,583,545 | 4/1986 | Towe | 128/630 |
| 4,590,427 | 5/1986 | Fukushima et al. | 324/318 |
| 4,664,129 | 5/1987 | Helzel et al. | 128/721 |
| 4,694,837 | 9/1987 | Blakeley et al. | 128/653 |
| 4,705,048 | 11/1987 | Pfohl | 128/715 |
| 4,793,356 | 12/1988 | Misic et al. | 128/653 |
| 4,805,622 | 2/1989 | Reidlinger et al. | 128/660.06 |

*Primary Examiner*—Lee S. Cohen
*Assistant Examiner*—Krista M. Pfaffle
*Attorney, Agent, or Firm*—Witherspoon & Hargest

[57] ABSTRACT

A stethoscope for use with nuclear magnetic resonance (NMR) screenings in order to supervise a patient, including a bell chest piece adapted to pick up audible heart and breathing sounds or other bodily sounds from the patient, a flexible hollow tube connected at one end thereof to the bell chest piece and adapted to transmit audible heart and breathing sounds from the bell chest piece. The novel features of the invention are, a microphone member adapted to be arranged at the opposite side the tube outside the zone of the maximum field strength of the NMR equipment and adapted to convert the acoustic signals into corresponding electrical signals, an optical transmitter to which the microphone member is connected and from which optical signals are transmitted to the surrounding in at least one direction, the optical signals corresponding to the electrical signals, and at least one receiver for receiving the optical signals from the optical transmitter and for converting the optical signals into electrical signals corresponding to said audible sounds.

9 Claims, 3 Drawing Sheets

STETHOSCOPE FOR USE IN NUCLEAR MAGNETIC RESONANCE DIAGNOSTICS

During recent years nuclear magnetic resonance (NMR) methods for imaging the internal organs of the human body have been widely spread. In NMR diagnostics the patient is subjected to a strong magnetic field which is temporarily as well as spatially varied. The patient is also subjected to an electrical field of radio, frequency and this field will produce nuclear spin resonance of certain elements, for example hydrogen. The final image achieved with this method is based on the hydrogen concentration in the various parts of the body.

When subjected to NMR diagnostics the patient is placed within a huge magnet the dimensions of which are in the order of $3 \times 3 \times 3$ m$^3$. The patient, resting on a patient's couch, is moved through a narrow tunnel until the organs to be examined are in the magnetical field of maximum strength. During such an investigation, which may last for several hours, the patient cannot be accessed for visual monitoring. NMR diagnostics of children is often performed with the child anaesthesized or sedated which pronounces the need for a simple and effective monitoring method. Certain manufacturers of NMR-equipment have provided their equipment with apparatuses for electrocardiogram recording. Compare for example European Patent EP No. 0 161 340 A1 to Siemens Aktiengesellschaft, Berlin. The E.C.G. electrodes and the conductors connected thereto are jammed by the strong magnetic field and the E.C.G. signal is often badly disturbed and difficult to interpret. Furthermore, the presence of metallic leads close to the imaging region may distort the images.

The object of the present invention is to provide a stethoscope by which the patient is monitored during NMR diagnostics, said stethoscope being so designed that the signals picked up therewith will not be disturbed by the electric and magnetic fields of the NMR equipment. The term stethoscope is commonly used for any device capable of transmitting bodily sounds from a patient to a doctor or nurse, regardless of the transmitting medium.

In accordance with another aspect of the present invention the stethoscope comprises a bell chest piece for picking up audible heart tones and breathing sounds or other bodily sounds, a conduit for transmitting said audible signals to microphone means generally outside the magnetic field of said NMR equipment and adapted to convert said audible signals into corresponding electrical signals, an optical transmitter connected to said microphone means for transmitting optical signals corresponding to said electrical signals in at least one predetermined direction and at least one receiver for receiving the optical signals from said transmitter and for converting said optical siganls into electrical signals corresponding to said audiable heart tones or other bodily sounds.

The stethoscope according to the invention permits remote monitoring of vital signs of a patient, i.e. cardiac and respiratory activity. Furthermore, it can be used for remote blood measurement, together with an ordinary blood pressure cuff and an elongated tube for detection of the so called Korotkoff sounds.

In accordance with a further aspect of the invention means are provided for converting the electrical signals of said receiver into audible signals.

Bell chest pieces per se are previously known from e.g. German patent specification No. 2 309 416 and U.S. Pat. Ser. No. 3,867,925.

Figure 2:
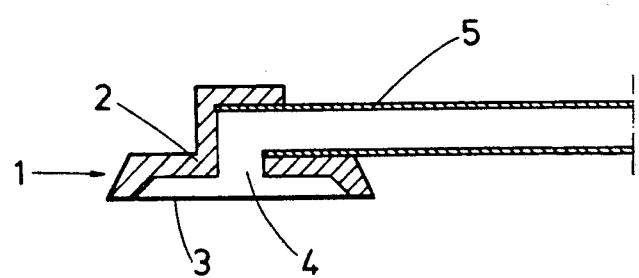
Figure 3:
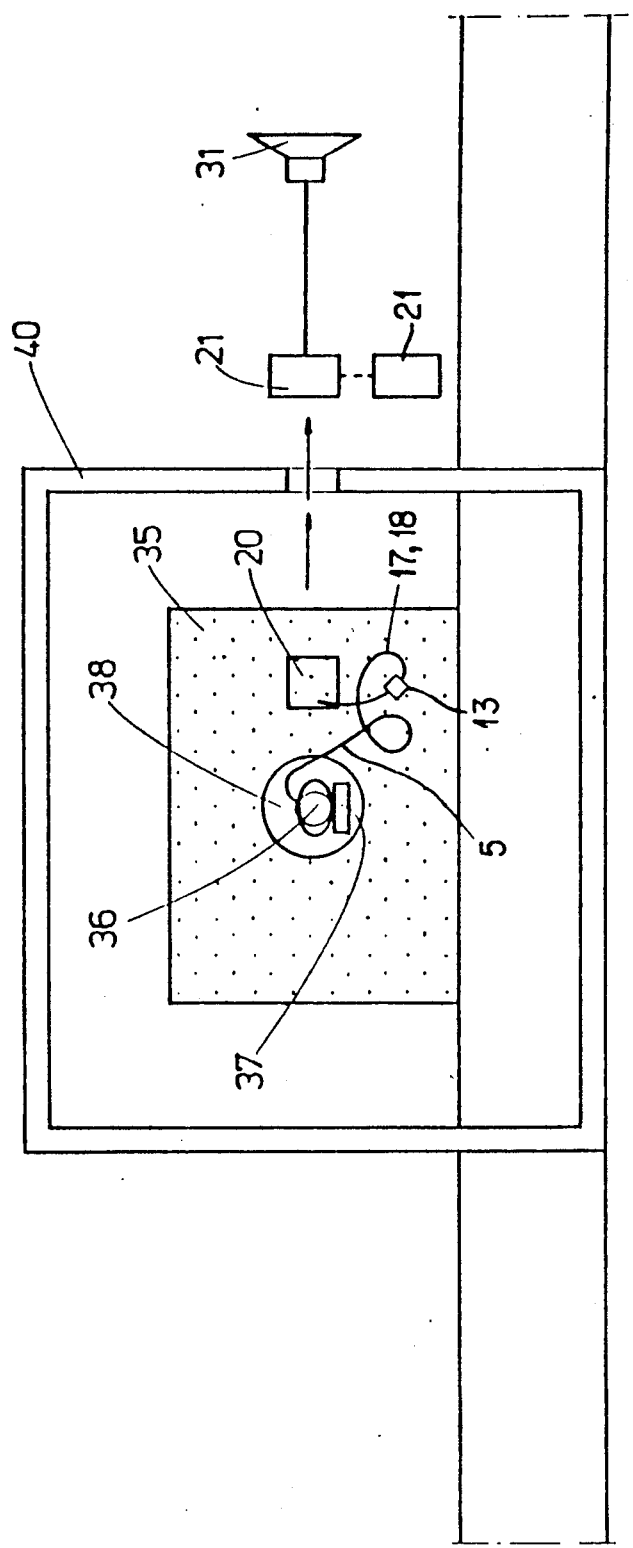
Figure 4:
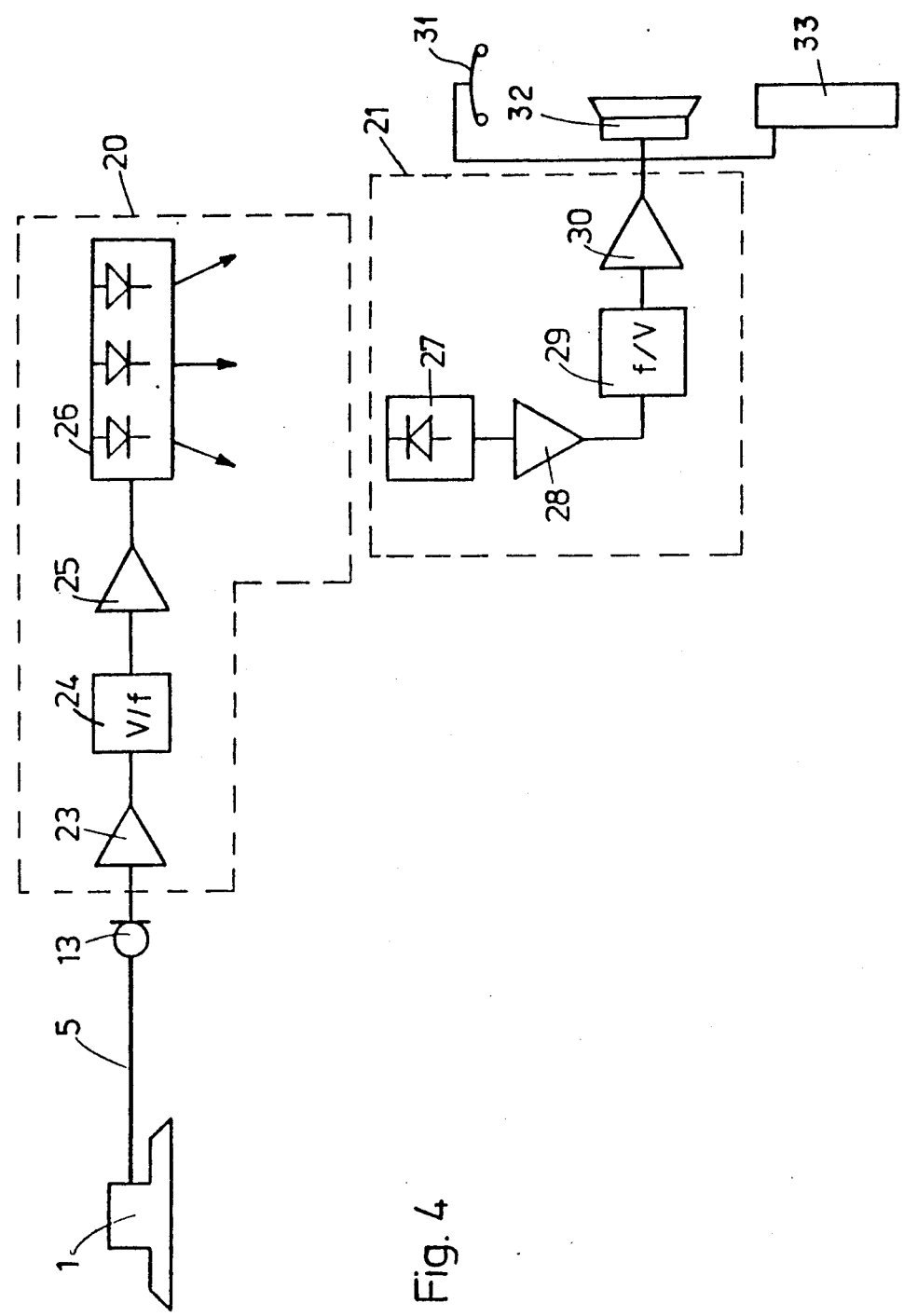

Further aspects of the invention will be described with reference to the accompanying drawings in which FIG. 1 is a top view of a bell chest piece forming part of the stethoscope in accordance with the invention, FIG. 2 a side sectional view of the bell chest piece and its microphone element, FIG. 3 is a simplified cross-sectional view of the NMR equipment and of the environment in which the stethoscope in accordance with the invention is used, and FIG. 4 is a block diagram of the transmitter and receiver units of the stethoscope in accordance with the invention.

As depicted in FIGS. 1 and 2, the stethoscope in accordance with the invention comprises a bell chest piece 1 comprising a housing 2, a membrane 3 and a cavity 4 formed between the membrane 3 and the bell chest piece housing 1. A flexible tube 5 attached to the upper portion of said bell piece 1 is in communication with said cavity 4. A pressure dressing 6, also referred to as a pressure bandage, is attached to the bell piece and comprises straps 7 and 8 which at one end thereof are attached to the upper portion of the bell piece and which at the opposite end thereof are provided with dressing attachment means in the form of a VELCRO strap comprising a hook tape 9 and a loop tape 10. Alternatively, the chest piece is simply resting by its own weight on the chest surface.

The pressure dressing 6, straps 7, 8, and hook and loop tape 9, 10 are shown in FIG. 1.

The opposite end of the tube 5 has an enlarged portion 12 housing a microphone 13 for effecting audible sounds as shown in FIG. 1. This microphone 13 is comprised of a transducer 14 converting the audible sound into electrical signals. Preferably the transducer 14 is of capacitor type, one plate 15 of which is of membrane and the other plate 16 which is stationary. Electrical conductors 17, 18 transmit the electrical signals to an optical transmitter unit 20 shown in FIGS. 3 and 4. Electrical signals from the transducer 14 are amplified in an amplifier 23 shown in FIG. 4 the output of which is connected to a voltage-to-frequency converter 24 converting the signal into a symmetric square wave the frequency of which varies in accordance with the audible signals around a predetermined carrier frequency, preferably in the range of 100 kHz, i.e. far above the frequency range of physiological heart and breath sounds. The output of the voltage-to-frequency converter 24 is connected to a drive circuit 25 for driving a number of transmitting diodes 26, preferably LED's transmitting infrared light in a wave length region of 950 nm. The LED's are preferably directed in different directions such that the light emitted in said directions is picked up by one or more receiver units 21 only one of which is shown in FIGS. 3 and 4. Each receiver unit comprises a photo diode 27 converting the optical signal into a frequency modulated electrical signal which is amplified in an amplifier 28 and converted into a voltage in a frequency-to-voltage converter 29 connected to the amplifier. The output of the frequency-to-voltage converter 29 is connected to an amplifier 30, the output of which is connected to an earphone 31 or a loudspeaker 32, and to monitoring equipment schematically shown at 33, and comprising for example an E.C.G. device, a cathode ray tube, and other appropriate recording and displaying devices.

The arrangement of the various parts of the stethoscope in accordance with the invention is depicted in FIG. 3. In FIG. 3 the NMR magnet is shown by reference numeral 35. The patient 36 is resting on a movable bed 37 which is brought into a narrow tunnel 38 of the NMR magnet. The bell chest piece 1, now depicted in FIG. 3, has been secured to the patient's body with the aid of the straps 7, 8 in a proper position at the patient's chest for picking up audible heart and breathing sounds. By applying the bell chest piece with pressure against the patient's body the level of the audible signals may rise by approximately 20 dB compared to a situation when the bell chest piece is applied without pressure against the patient's body.

The pressure variations appearing in the cavity 4 of the bell chest piece 1 depicted in FIG. 2 are transmitted via the flexible tube 5 to the transducer 14 which during the screening must not be present in the vicinity of the patient since if it were, then it would pick up interfering electromagnetical signals generated by the NMR equipment. Therefore this transducer has to be placed outside the tunnel 38 and accordingly the length of the tube 5 has to be generally at least 2 m. The audible signals are picked up by the membrane 3 in combination with the air volume confined in the cavity 4 and the air lumen of the tube 5. The sensitivity to pick up audible signals is inversely related to the air volume of the cavity and of the tube. From an anatomic point of view the bell chest piece should have a diameter of about 25-50 mm for adults and the membrane 3 is preferably a glass fibre reinforced epoxy plate having a thickness in the order of about 0.2-0.6 mm. The tube 5 is preferably a thick walled tube of polyvinyl chloride. Its inner diameter is in the order of 1-3 mm and depends on the material selected for the tube. The influence of the tube 5 on the audible signal can be described from the general theory of transmission lines. The tube 5 has a characteristic acoustic impedance determined by the density, compressibility and viscosity of air and of the elastic and viscoelastic properties of the tube material. A certain degree of mismatch will exist at the two ends of the tube. This mismatch will give rise to sound reflexions distorting the audible signal and rendering the analysis of the signal difficult. In an ordinary, conventional stethoscope with a tube length of about 50 cm the tube will be at resonance for an audible signal having a frequency of about 150 Hz. If the tube is made longer the frequency at which it resonates will decrease. As with transmission lines the tube 5 will also be resonant for audible sounds at higher frequences corresponding to higher order harmonics of the resonance frequency. The above mentioned characteristics are purely dispersive, i.e. the signal power is redistributed in the frequency plane without any losses. However, there are also losses present caused by the flow resistance of the tube. The viscous resistance of the tube filled with a viscous medium, e.g. air, is inversely related to the fourth order of the tube diameter. Accordingly, it is important that the wall of the tube is not made too thin. The flow resistance is also proportional to the length of the tube and accordingly the tube should be as short as possible. On the other hand, the NMR equipment puts restrictions on this matter. The patient is normally moved into and out of the magnet resting on a bed in the form of a couch or sledge. This means that the bell chest piece 1 must be fastened on the patient's chest with the couch in its position outside the tunnel. The audible signal must not be deteriorated and must be possible to monitor when the patient is inside the tunnel. Therefore, the length of the tube must generally be in the order of at least 2 m.

To summarize, the tube 5 should be as short as possible and there is an optimum internal diameter. This optimum internal diameter is dependent on the length of the tubing and on the specific material of the tubing but is generally in the order of between 1-3 mm.

The NMR magnet and its peripheral equipment is normally enclosed by an electro magnetic shielded room 40. This shielded room 40 on the one hand prevents extraneous signals from interfering with the electric and magnetic fields generated by the NMR apparatus and on the other hand prevents said electrical and magnetical fields from escaping. Normally all monitoring equipment is located outside the shielded room 40. Normally there is also an inspection window provided in one of the walls of the room and therefore no additional means, such as conductors, need to be installed in order to transfer the signals from the transmitter 20 to the receiver 21 located outside the screening room. If desired, the receiver 21 can be located at different places outside of the shielded room.

The above described embodiment of the invention may be modified and varied. May be used in order to improve the frequency response. The use of a liquid will however present practical problems because air bubbles must not be present in the liquid.

We claim:

1. A stethoscope system for monitoring a patient in conjunction with investigations using an NMR magnet, said system comprising:

an NMR magnet having a patient accommodating tunnel which in operation contains electric and magnetic fields;

a bell chest piece positioned within said tunnel and adapted to be placed on the patient's skin in order to pick up audible heart and breathing sounds;

a microphone positioned outside of said tunnel;

a flexible hollow tube of dielectric material with a first and a second end, said first end being connected to said bell chest piece and said second end being connected to said microphone, said microphone being adapted to convert said audible heart and breathing sounds into electrical signals;

an optical transmitter positioned outside of said tunnel and electrically connected to said microphone and adapted to convert said electrical signals into corresponding optical signals, and receiver means for receiving said optical signals in order to allow monitoring of the patient by observers.

2. A stethoscope system for monitoring a patient in conjunction with investigations using an NMR magnet, said system comprising:

a bell chest piece adapted to be placed on the patient's skin in order to pick up audible heart and breathing sounds, a flexible hollow tube with a first and a second end, said first end being connected to said bell chest piece, a microphone connected to the second end of said hollow tube and adapted to convert said audible heart and breathing sounds into electrical signals, an optical transmitter electrically connected to said microphone and adapted to convert said electrical signals into corresponding optical signals, and receiver means for receiving said optical signals in order to allow monitoring of the patient by observers, said hollow tube being of dielectric material and having a length permitting extension of said hollow tube from said bell chest piece within electric and magnetic fields of said NMR magnet to said microphone and said optical transmitter placed outside said NMR magnet.

3. A stethoscope system in accordance with claim 2 wherein said hollow tube has a length in the order of at least 2 meters and an inner diameter in the range of about 1 mm to about 3 mm.

4. A stethoscope system in accordance with claim 2, wherein said optical transmitter comprises a voltage-to-frequency converter for converting said electrical signals into a frequency modulated train of pulses.

5. A stethoscope system in accordance with claim 2, wherein said optical transmitter comprises light emitting diodes emitting optical signals in the infrared wavelength region.

6. A stethoscope system in accordance with claim 5, wherein said light emitting diodes are directed in different directions.

7. A stethoscope system in accordance with claim 5 for use in an electrically shielded room in which is housed said NMR magnet, said room including at least one window for transmitting said optical signals, said receiver means for receiving said optical signals outside of said room.

8. A stethoscope sytem in accordance with claim 2 wherein said receiver means comprises means for converting said electrical signals corresponding to said audible heart and breathing sounds into audible sound.

9. A stethoscope system in accordance with claim 8 wherein said receiver means comprises one output adapter for connection to ear phones and another output adapter for connection to a display unit for displaying said electrical signals corresponding to said audible heart and breathing sounds.

* * * * *